United States Patent [19]

Jawish

[11] Patent Number: 4,942,872
[45] Date of Patent: Jul. 24, 1990

[54] EXTERNAL FASTENER FOR BONES AND JOINTS

[76] Inventor: Robert Jawish, 146 rue Lourmel, Paris, 75015, France

[21] Appl. No.: 889,934
[22] PCT Filed: Oct. 7, 1985
[86] PCT No.: PCT/FR85/00280
   § 371 Date: Jul. 7, 1986
   § 102(e) Date: Jul. 7, 1986
[87] PCT Pub. No.: WO86/02821
   PCT Pub. Date: May 22, 1986

[30] Foreign Application Priority Data

Nov. 15, 1984 [FR] France ............................ 84 17415

[51] Int. Cl.⁵ ...................... A61B 17/60; F16C 11/00
[52] U.S. Cl. .................................................. 606/57
[58] Field of Search ........... 128/92 Z, 92 ZZ, 92 ZY, 128/92 ZK, 92 ZW, 92 VY, 92 VV, 92 VW, 83, 84 B, 88

[56] References Cited

U.S. PATENT DOCUMENTS 1,997,466  4/1934  Longfellow .
2,251,209  2/1940  Stader .
2,439,995  4/1944  Thraikill .
4,308,863  1/1982  Fischer ........................... 128/92 ZZ
4,475,546  10/1984  Patton ............................ 128/92 ZZ
4,621,627  11/1986  DeBastiani et al. ............. 128/92 Z

FOREIGN PATENT DOCUMENTS 0140786  5/1985  European Pat. Off. .
2825481  12/1979  Fed. Rep. of Germany .
0789882  8/1935  France .
2317717  2/1977  France .
2353271  12/1977  France .
2397826  2/1979  France .
194246  9/1967  U.S.S.R. ........................... 128/92 Z
1146017  3/1985  U.S.S.R. ........................... 128/92 Z
0029174  1/1913  United Kingdom .

Primary Examiner—Stephen C. Pellegrino
Assistant Examiner—Ralph Lewis
Attorney, Agent, or Firm—Sandler, Greenblum & Bernstein

[57] ABSTRACT

A device for externally fixing bones and joints. The device is made of multiple connectable cylindrical sleeves, each housing a hollow cylindrical member. Both the cylindrical sleeves and their internal cylindrical members are provided with holes in their cylindrical walls, for insertion of bone-anchoring pins.

35 Claims, 8 Drawing Sheets

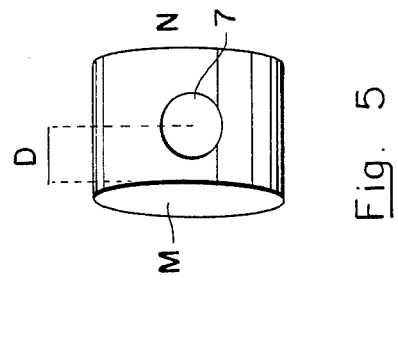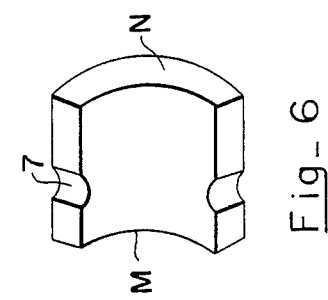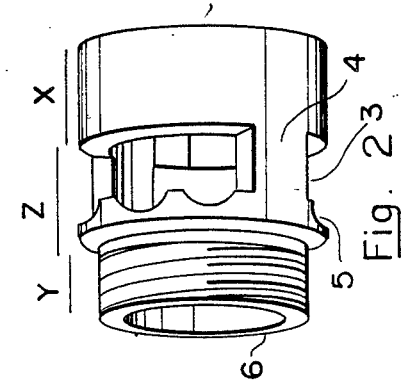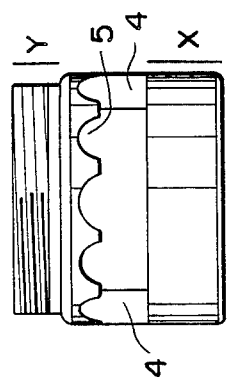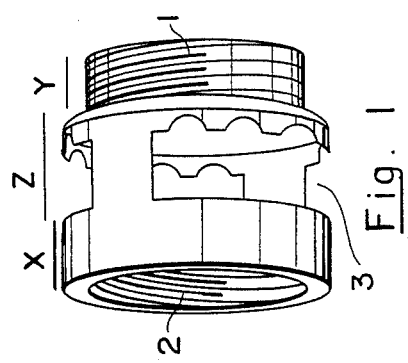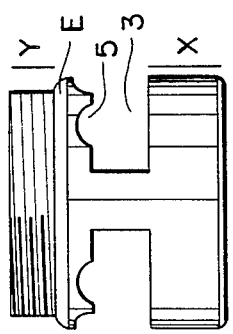
Fig. 1
Fig. 2
Fig. 3
Fig. 4
Fig. 5
Fig. 6

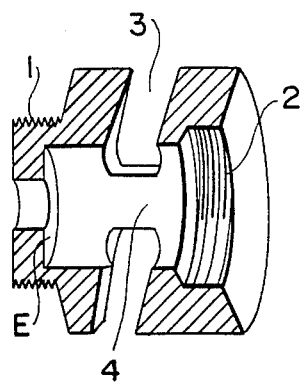
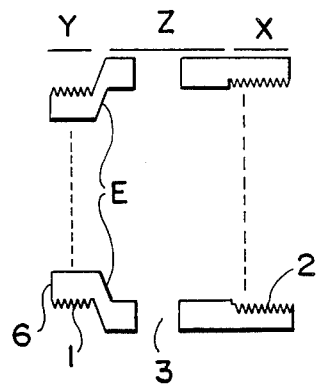
Fig. 7   Fig. 8
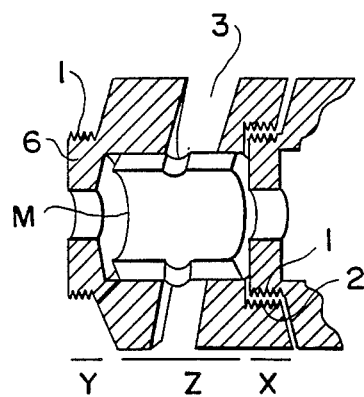
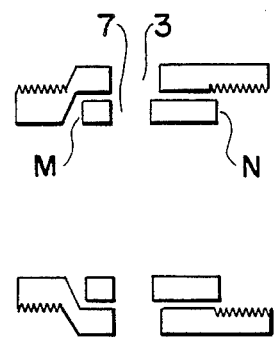
Fig. 9   Fig. 10

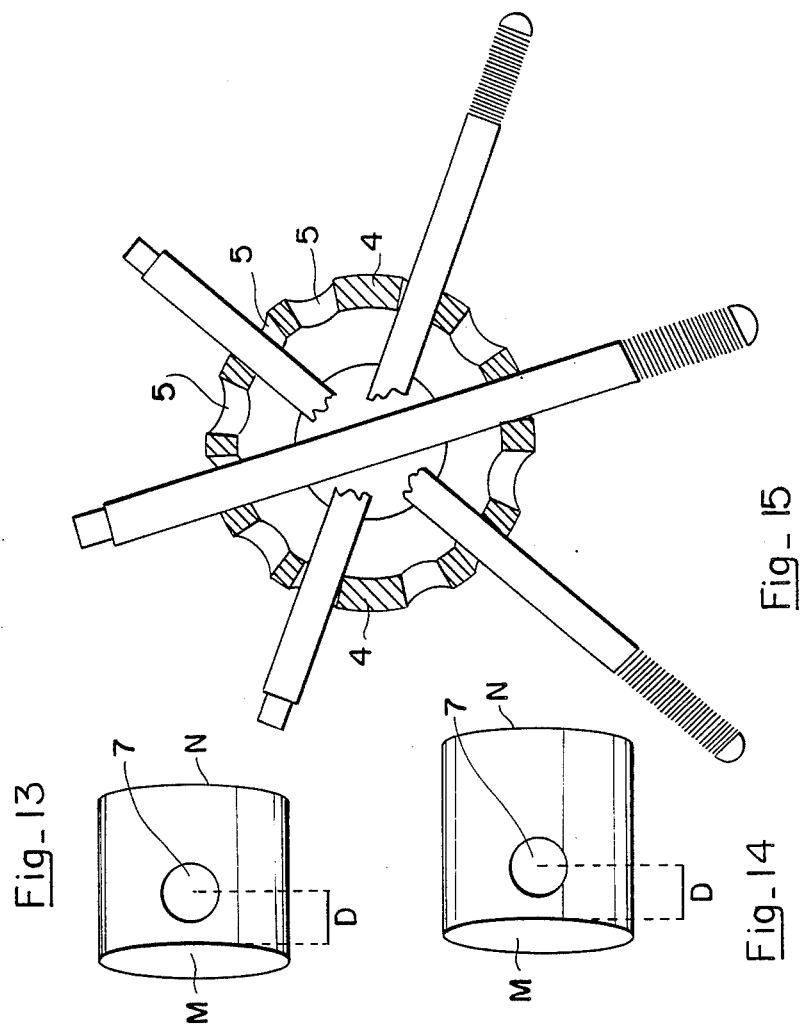
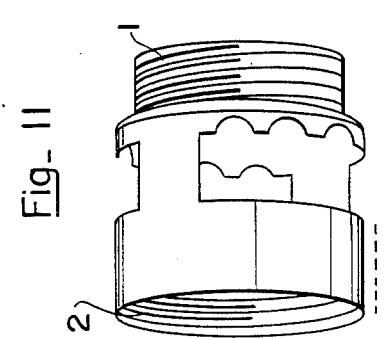
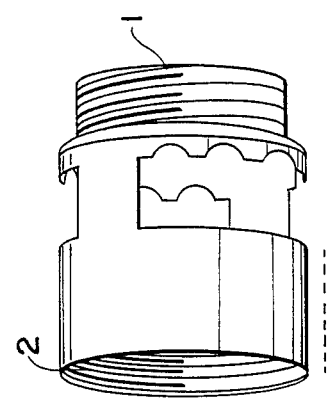

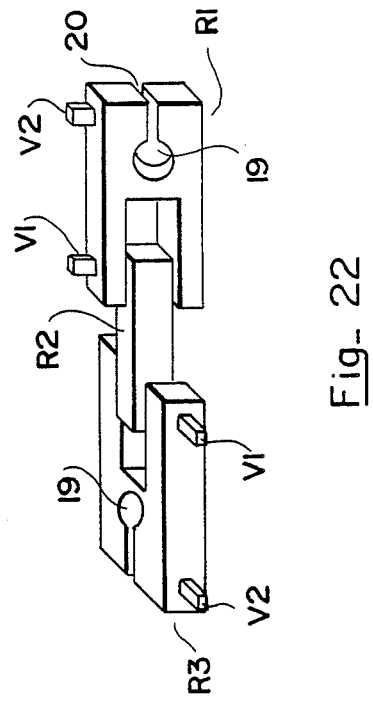
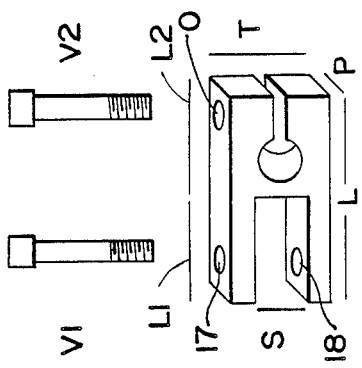
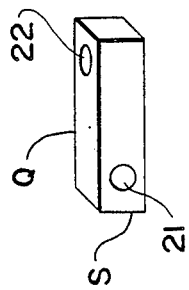
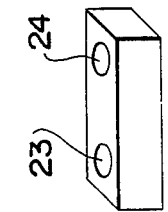

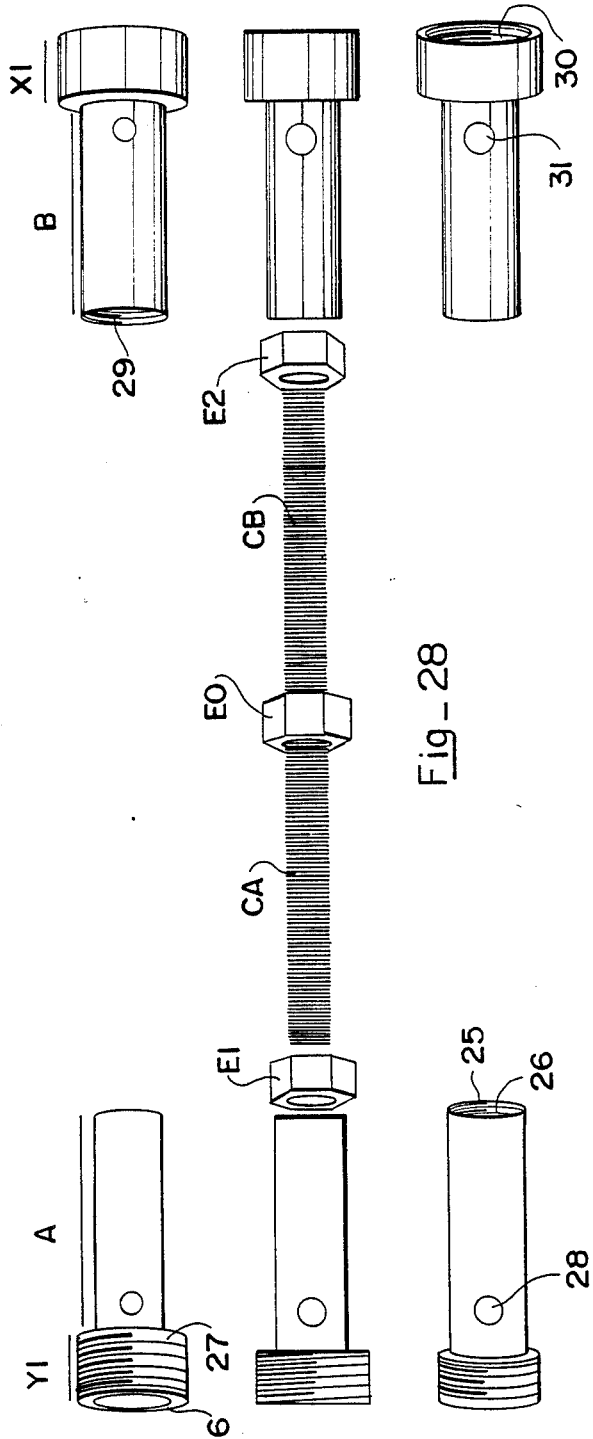

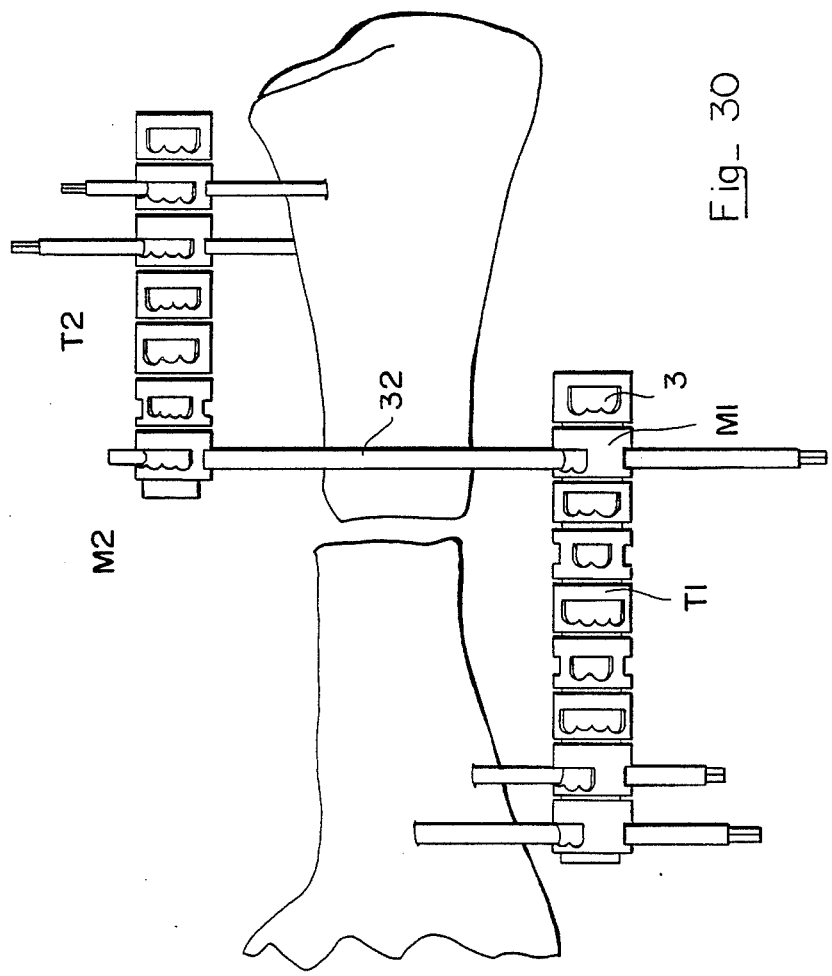

EXTERNAL FASTENER FOR BONES AND JOINTS

BACKGROUND OF THE INVENTION

1. Field of the Invention

The present invention relates to a device for externally setting bones and joints, by the compression or distraction of bone fragments.

2. Description of the Prior Art

Various devices for externally setting bones are known in the art; all of these devices have disadvantages of one type or another. One such device, a rigid tubular device, cannot be used in different positions. Other devices can be used in different positions; however, because they comprise multiple connected pieces, and are of considerable complexity, these devices are too heavy, and lack sufficient strength for their intended purpose.

The device of the present invention overcomes the indicated deficiencies of the devices of the prior art. It comprises a solid tubular device which can be easily manipulated, and is well suited for placing in various positions covering different spacial arrangements. It is also superior by virtue of being lighter in weight than the devices of the prior art.

SUMMARY OF THE INVENTION

The device of the present invention is a compression system, available for use wherever needed, and is capable of applying a significant compression force against bones. The device comprises a rigid tubular tutor, or guide, for bone-anchoring members, such as bone-contacting pins; the guide permits such pins, passing through the guide, free rotation around the guide perpendicular to its axis, thereby allowing each pin to be fixed in the proper position.

BRIEF DESCRIPTION OF THE DRAWINGS

FIG. 1 is a perspective view of the cylindrical sleeve of the tubular guide of the present invention.

FIG. 2 is a perspective view of the sleeve of FIG. 1 from a different angle.

FIG. 3 is a side elevation view of the sleeve of FIG. 1.

FIG. 4 is another side elevation view of the sleeve of FIG. 1.

FIG. 5 is a perspective view of the internal cylinder of the present invention.

FIG. 6 is a partial cross-sectional view of the internal cylinder of FIG. 5, along its axis.

FIG. 7 is a perspective cross-sectional view of the sleeve of FIG. 1.

FIG. 8 is an elevational cross-sectional view of the sleeve FIG. 1.

FIG. 9 is a perspective cross-sectional view of two successively connected cylindrical sleeves, one housing an internal cylinder to form a tubular guide of the present invention.

FIG. 10 is an elevation cross-sectional view of the sleeves and cylinder shown in FIG. 9.

FIG. 11 is a perspective view of a second embodiment of the cylindrical sleeve.

FIG. 12 is a perspective view of a third embodiment of the cylindrical sleeve.

FIG. 13 is a perspective view of a second embodiment of the internal cylinder, corresponding to the cylindrical sleeve of FIG. 11.

FIG. 14 is a perspective view of a third embodiment of the internal cylinder, corresponding to the cylindrical sleeve of FIG. 12.

FIG. 15 is a top plan view of the cylindrical sleeve of the present invention, showing the capability of the sleeve for receiving the bone-anchoring pin inserted therethrough in various positions;

FIG. 21 is a perspective view of a terminal element for the tubular guide of the present invention.

FIG. 22 is a perspective view of the joint of the present invention.

FIG. 23 is a perspective view of a lateral member of the joint, and of two screws for insertion therein.

FIG. 24 is one embodiment of the linking member of the joint.

FIG. 25 is a second embodiment of the linking member.

FIG. 26 is a perspective view of one of the brackets of the compressor-distracter of the present invention.

FIG. 27 is a perspective view of the other of the brackets of the compressor-distracter.

FIG. 28' is a perspective view of the device of the invention, in use for setting bones, wherein the tubular guide consists of successively connected cylindrical sleeves.

FIG. 30 is an alternative embodiment of the device in use.

DESCRIPTION OF THE PREFERRED EMBODIMENTS

The tubular guide of the device of the invention comprises standard sleeves of the type shown in FIG. 1; each sleeve comprises a hollow cylinder, having threaded edges for successive connection of multiple sleeves to one another.

Specifically, each sleeve is a hollow cylinder pearled by an anterior, or front extremity X and by a posterior, or rear extremity Y, these two extremities being connected by section Z.

As shown in FIG. 8, the external diameter of front extremity X, and the external diameter of section Z, are both greater than the external diameter of rear extremity Y. Further, the internal diameter of front extremity X is greater than the internal diameter of section Z, and the internal diameter of section Z is greater than the internal diameter of rear extremity Y. Shoulder E is situated between rear extremity Y and section Z.

Figure 28:
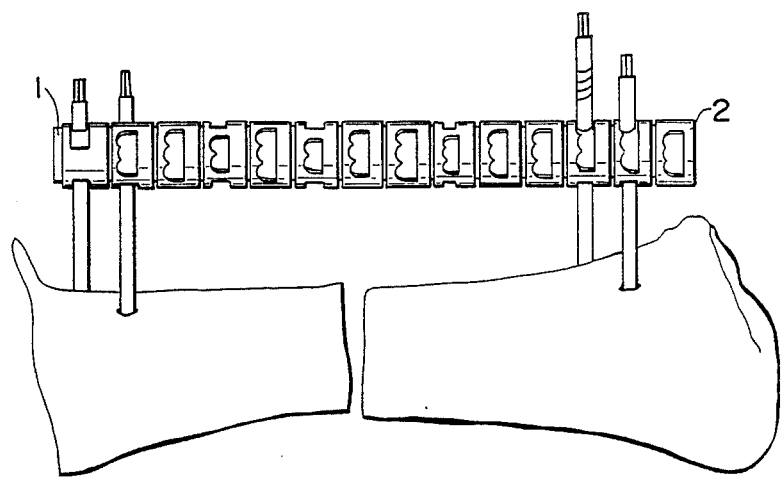
FIG. 28 is a perspective view of the tension screw, and of the fixed screw-nut and the mobile nuts mounted on the tension screw.

Front extremity X comprises internal thread 2, and rear extremity Y comprises external thread 1. The diameter of external thread 1 is less than that of internal thread 2, thereby permitting threaded connection of successive sleeves by their respective threads 1 and 2, as shown in FIG. 28, to form the tubular guide.

As shown in FIGS. 3, 4, and 7, the sleeve further defines circumferential slot 3 spanned by two budges 4. Bridges 4 join front extremity X and rear extremity Y.

As shown in FIG. 15, slot 3 allows a pin to pass through the sleeve, and to rotate around the sleeve, perpendicularly to the axis of the sleeve, before the pin is screwed into bone. The pin is screwed into bone by means of thread 9, shown in FIG. 16.

The edge of slot 3 is provided with several semicircular notches 5. As shown in FIG. 28, these notches are sized according to the diameter of the pin, and serve to receive the pin, to be lodged and locked into the necessary position.

FIG. 5 shows a hollow cylinder provided with front edge M and rear edge N. FIG. 6 shows a sagittal section of this cylinder along its axis. This cylinder is characterized by a predetermined thickness, and by both length and diameter less than that of the sleeve. The length of this cylinder is equal to that of section Z, and its external diameter is comparable to the internal diameter of section Z. This cylinder may thereby be housed in section Z of the sleeve as an internal cylinder, situated between threaded edges 1 and 2, and may rotate freely within the sleeve around the sleeve's axis.

This internal cylinder is provided with two diametrically opposed holes 7, which appear through slot 3 whenever the cylinder is housed within the sleeve. Both holes 7 have a diameter equal to that of the transbone pin, and are situated at distance D from front edge M of the internal cylinder; distance D is less than half of the length of the internal cylinder.

As shown in FIGS. 9 and 10, holes 7 are visible through slot 3 when the internal cylinder is housed in the sleeve. Accordingly, a pin, when inserted into slot 3 perpendicularly to the axis of the sleeve, can pass through slot 3, and through both holes 7, in a path perpendicular to the common axis of the sleeve and of the internal cylinder; the pin, which may be provided with a thread, may be passed through slot 3 and holes 7 to contact the bone.

Prior to being screwed into the bone, a pin inserted through slot 3 and through holes 7 of the internal cylinder may be rotated freely around the axis of both the sleeve and the cylinder. Such rotation correspondingly compels the cylinder also to rotate; as shown in FIG. 15, rotating the pin in this manner leads the pin past notches 5 of slot 3; such rotation of the pin is limited on each side of the sleeve by bridges 4.

As shown in FIG. 10, the presence of a pin inserted through the sleeve, and through the internal cylinder housed therein, prevents front edge M of the internal cylinder from contacting shoulder E. The pin is lodged in one of the notches provided in slot 3, thereby preventing the internal cylinder from advancing closer to rear extremity Y. As a result, rear edge N of the internal cylinder extends into front extremity X; the pin is accordingly fixed in the bone at a predetermined angle.

Pins may be screwed into the bone at the required position by means of a brace, or, alternatively, may be screwed into a forward bore made by a bit. As shown in FIG. 9, a pin is locked into place in the sleeve through which it has been inserted by connection of the sleeve to another sleeve.

Successive connection of a second sleeve to a first sleeve causes surface 6 of second sleeve rear extremity Y to engage rear edge N of the internal cylinder housed in the first sleeve; threaded connection of the two sleeves will thereby advance the internal cylinder housed in the first sleeve toward shoulder E of the first sleeve.

When a first sleeve and second sleeve are connected, surface 6 of the externally threaded rear extremity Y of the second sleeve pushes against the internal cylinder of the first sleeve; a pin in the first sleeve is accordingly immobilized by this internal cylinder in requisite notch 5 of the first sleeve. In this manner, where a pin is provided in a sleeve for implantation in the bone, the pin can be secured in the proper position simply by connection of the sleeve through which it has been inserted to a successive sleeve.

The use of both sleeve and internal cylinder permits the assembly of a rigid tubular guide, or tutor, whose length can be modified as required; as shown in FIG. 28, this configuration further provides for orientation of each pin according to the position of bone fragments.

Accordingly, a straight tutor can be used to set non-aligned bone fragments. The same guide is suitable for setting two long bones.

As shown in FIG. 28', pins can be rotated within the tubular guide to allow for different positioning of such pins, in various angles. Because the pins can be rotated in this manner in the tubular guide, a single pin can be used to connect two independent guides without intermediate articulation being required.

A particular example of this capability is provided in FIG. 30, which shows connecting bar or pin 32 securely joining two straight tubular guides $T_1$ and $T_2$, situated in two different planes, without requiring any joints. One end of pin 32 is secured in sleeve $M_1$ of tubular guide $T_1$, with the other end being secured in sleeve $M_2$ of tubular guide $T_2$.

The configuration of elements shown in FIG. 30 may be provided by first securing pin 32 in sleeve $M_1$, of tubular guide $T_1$. After pin 32 is secured in guide $T_1$, in this manner, pin 32 may then be secured in sleeve $M_2$ of tubular guide $T_2$.

Multiple tubular guides, situated in different planes, can be connected in similar fashion. Accordingly, a system of multiple connected tutors can be provided without the need for supplemental connective apparatus, which can cause the bone setting to be fragile.

FIG. 11 shows another embodiment of the cylindrical sleeve, differing from the embodiment shown in FIGS. 1-4 in that front extremity X is longer in the embodiment of FIG. 11 than in the embodiment of FIGS. 1-4. The greater length of front extremity X increases the distance between two adjacent pins where such two pins, secured in separate tubular guides, converge at a single point in the bone.

FIG. 12 shows yet a third embodiment of the cylindrical sleeve, characterized by front extremity X being still longer than front extremity X of the embodiment shown in FIG. 11.

FIGS. 13 and 14 show internal cylinders corresponding to the cylindrical sleeves of FIGS. 11 and 12, respectively. For each such cylinder, hole 7 is positioned at fixed distance D from front edge M.

Figure 16:
FIG. 16 is a side elevational view of a bone-anchoring pin of the present invention.
Figure 17:
FIG. 17 is a side elevational view of a second embodiment of the bone-anchoring pin.

FIGS. 16 and 17 show different embodiments, varying in diameter and length, of the pin to be secured in the tubular guide of the device of the invention. As shown specifically in FIG. 16, the pin may be provided with point 8; point 8 is followed by thread 9, which may be any of various lengths. The other end of the pin is provided with rectangular tip 10, followed by neck 1 of lesser diameter. Neck 11 may serve as a grip for a brace utilized to drive the pin into the bone.

Figure 18:
FIG. 18 is a side elevational view of the connecting bar of the present invention.

FIG. 18 shows a connecting bar. This bar may be any of various

Figure 19:
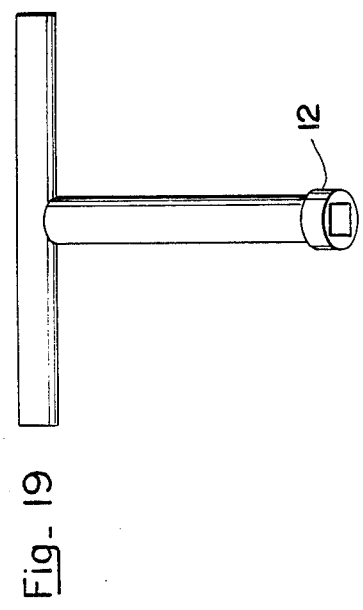
FIG. 19 is a perspective view of the T-shaped key for adjusting the joint screws of the present invention.

FIG. 19 shows a T-shaped key. The base of the T is provided with square gap 12 for engaging screws $V_1$ and $V_2$ of the joint shown in FIG. 22.

Figure 20:
FIG. 20 is a side elevational view of a third embodiment of the bone-anchoring pin.

FIG. 20 shows a pin of any of various dimensions, provided with smooth tip 13, and with thread 15, also of varying length. This pin requires a bore already provided in the bone for insertion; it may be screwed into the bone by the T-shaped key shown in FIG. 19.

FIGS. 21–25 show supplemental connective elements which are appropriate for the device of the invention where such apparatus is required to overcome certain technical difficulties.

FIG. 21 shows a terminal element provided, at one end, with thread 1 for connection to the terminal sleeve in the tubular guide. This terminal element comprises cylindrical section K, situated between bar W and end section $Y_2$.

Bar W extends along the axis of cylindrical section K, in a direction perpendicular to the surface of a cylindrical cross-section of cylindrical section K. Bar W serves to attach the terminal element of FIG. 21 to the joint shown in FIG. 22.

End section $Y_2$, provided with external thread 1, has a diameter corresponding to that of rear extremity Y of a cylindrical sleeve; like rear extremity Y, section $Y_2$ is also threadedly connectable to front extremity X of a cylindrical sleeve. Orifice 6 may be used to tighten the connection between end section $Y_2$ and extremity X of a cylindrical sleeve.

The joint shown in FIG. 22 is a "kneecap" joint, comprising three aligned articulated elements interconnected by two pivotal axes; specifically, lateral members $R_1$ and $R_3$, which are substantially identical, are joined by intermediate, or linking member $R_2$.

As shown in FIG. 23, each of lateral members $R_1$ and $R_3$ is a parallelepipedon, characterized by rectangular sections of length L, width P, and thickness T.

Each of lateral members $R_1$ and $R_3$ is provided, at one of its extremities, with orifice 19, perpendicular to the axis of screw $V_1$. Connecting orifice 19 to the front edge of each lateral member is slit 20, for receiving a connecting bar.

Slit 20 is tightened by means of screw $V_2$, aligned perpendicularly to slit 20. Specifically, screw $V_2$ passes through orifice O, which intersects segment $L_2$ perpendicular to the plane in which slit 20 L is situated. Screw $V_2$ serves to tighten orifice 19 on a connecting bar inserted therein.

Both screw $V_1$ and screw $V_2$ are threaded at their distal ends for tightening in their respective orifices.

The other extremity of each of lateral members $R_1$ and $R_3$ is characterized by a gap of length L, width P, and width S, for receiving linking member $R_2$. Linking member $R_2$ is hinged to each of lateral members $R_1$ and $R_3$ in its gap, through orifices 17 and 18, by screw $V_1$; orifice 18 as internally threaded. This arrangement allows for the articulation of these members.

Linking member $R_2$ is a parallelepipedon with two sets of rectangular opposed lateral faces of length Q, and opposed square terminal surfaces having sides of length S. Orifices 21 and 22 are provided at each end of linking member $R_2$ to allow the previously discussed articulation with lateral members $R_1$ and $R_3$.

FIG. 24 shows one embodiment of linking member $R_2$, wherein orifices 21 and 22 are situated on lines which are perpendicular and non-intersecting.

In another embodiment of linking member $R_2$, shown in FIG. 25, orifices 23 and 24 are aligned in a single plane, through opposed faces of linking member $R_2$; this configuration provides for articulation of lateral member $R_1$ and $R_3$ in a single plane. One of lateral members $R_1$ and $R_3$ can receive bar W in its orifice 19. The other of these two lateral members can receive a connecting bar secured in another joint which is connected to a separate tubular guide.

Thus, the two orifices 19, of respective lateral member $R_1$ and $R_3$ in a particular joint, can be aligned either in perpendicular or in parallel, depending upon whether orifices 23 and 24 of linking member $R_2$ are aligned in perpendicular or in parallel. Depending upon different dispositions of the joint, the multiple possible configurations of elements allow a wide variety of possible connections between different tubular guides. The joint is secured in position by screws $V_1$ and $V_2$, in the manner previously discussed.

The previously discussed terminal element of FIG. 21, and the joint of FIG. 22, can be provided at the extremity of each tutor, or tubular guide, to facilitate connection. Two joints can be joined by a connecting bar. Each joint can be varied according to the intermediate pieces of which it is constructed, thereby permitting two assembled joints considerable spacial mobility.

The device of the invention may include a compressor-distracter situated along the axis of the tubular guide. In this position, the compressor-distracter may be used to impart a significant tractor force to the compression system.

As shown in FIGS. 26–28, the compressor-distracter comprises three principal elements and two nuts. Specifically, the compressor-distracter includes two lateral, cylindrical hollow brackets, each provided with an internal thread. Each of these cylindrical brackets has an extremity externally threaded for connection to the threaded edges of tubular guide sleeves.

FIG. 26 shows one of these brackets, comprising hollow cylinder A, characterized by wall 25. Wall 25 is of a specific thickness, and is provided with longitudinal, internal thread 26. One end of the bracket comprises adjustment edge $Y_1$.

Figure 29:
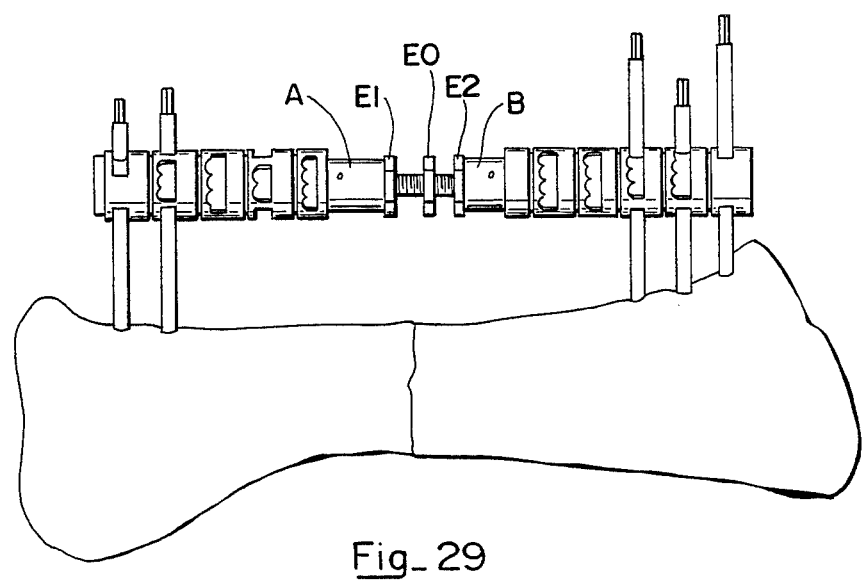
FIG. 29 is a perspective view of the device of the invention, in use for setting bones, incorporating a compressor-distracter for connecting cylindrical sleeves.

Adjustment edge $Y_1$ is provided with external thread 27, and has the same diameter as rear extremity Y of a tubular guide cylindrical sleeve, thereby permitting connection with the tubular guide. Specifically, as shown in FIG. 29, this bracket of the compressor-distracter can be threadedly connected by means of adjustment edge $Y_1$, with front extremity X of a tubular guide cylindrical sleeve.

FIG. 27 shows a second bracket, comprising hollow cylinder B. Hollow cylinder B is identical to hollow cylinder A, except in being provided with internal thread 29, which is opposed to internal thread 26 of hollow cylinder A.

Outer end $X_1$ of this second bracket has the same diameter as front extremity X of a tubular guide cylindrical sleeve. Accordingly, as shown in FIG. 29, this second bracket can be threadedly connected by means of outer end $X_1$ to rear extremity Y of a tubular guide cylindrical sleeve.

Cylinders A and B are provided, respectively, with orifices 28 and 31, suitable as supports for tightening the brackets.

FIG. 28 shows an axial member, or tension screw, which may also be referred to as an intermediate tension screw, externally and longitudinally threaded along its entire length. The tension screw serves as an intermediate element for connection of the cylindrical brackets of the compressor-distracter. This tension screw is provided with opposed extremities for threaded connection with the interior of the cylindrical brackets along the common axis of these brackets and the tension screw.

For receiving the threaded, opposed extremities of the tension screw, the two cylindrical brackets are, as indicated, internally threaded with opposed threads 26 and 29, respectively. Corresponding to the opposed threading of the two cylindrical brackets, the tension screw is provided with opposed threaded sections CA and CB, separated by fixed screw-nut EO.

Accordingly, turning the tension screw in one direction will direct force toward the cylindrical brackets and their respective tubular guides. The result will be compression of the bone fragments, respectively associated with each of these cylindrical brackets, along the axis of the tubular guide. Correspondingly, turning the tension screw in the opposite direction will cause distraction, thereby withdrawing these cylindrical brackets.

As shown in FIG. 29, mobile nuts $E_1$ and $E_2$ are situated on the tension screw. Each is in contact with one of the cylindrical brackets at its extremity, thereby preventing the three aligned members of the compressor-distracter from unwanted movement in relation to one another.

I claim:

1. A device adapted to be used externally for fixing bones and joints of a patient, comprising:
   (a) a plurality of cylindrical sleeves, each comprising a cylindrical wall provided with holes for receiving a bone-anchoring member therethrough, and each including a front extremity and a rear extremity, said sleeves being releasably connectable to one another in succession by connecting said rear extremity of a first one of said sleeves with said front extremity of a second one of said sleeves in order to form a tubular tutor; and
   (b) a plurality of hollow cylindrical members, one houseable in each of said sleeves, each comprising a cylindrical wall provided with holes for receiving a bone-anchoring member therethrough.

2. The device of claim 1, further comprising a joint means connectable to a terminal sleeve in said tubular tutor for articulating said tubular tutor about a knee of a patient.

3. The device of claim 2, wherein said joint means comprises a plurality of lateral members pivotally connected to a linking member for linking said lateral members, said linking member having a substantially square cross-section and comprising a plurality of orifices for receiving screws to connect said lateral members to said linking member.

4. The device of claim 3, wherein said plurality of orifices comprise two orifices oriented perpendicularly to one another.

5. The device of claim 3, wherein said plurality of orifices comprise two orifices oriented parallel to one another.

6. The device of claim 3, wherein at least one of said lateral members comprises a first portion and a second portion, said first portion comprising a first hole connected to a slit.

7. The device of claim 6, wherein said second portion comprises a plurality of arms defining a space therebetween, said space extending substantially through the thickness of said at least one lateral member.

8. The device of claim 7, wherein at least one of said arms comprises a second hole for receiving a screw to connect said at least one lateral member with said linking member.

9. The device of claim 8, wherein said first portion further comprises a third hole extending perpendicularly to said first hole.

10. The device of claim 9, wherein said second hole and said third hole extend parallel to each other.

11. The device of claim 10, wherein said orifices are located on a common surface of said linking member.

12. The device of claim 1, wherein each of said cylindrical sleeves comprises a front portion including said front extremity, a rear portion including said rear extremity, and a middle portion disposed between said front portion and said rear portion, each of said front portion, said middle portion, and said rear portion comprising an internal surface and an external surface.

13. The device of claim 12, further comprising an end member adapted to be screwed onto said rear portion of one of said cylindrical sleeves positioned at a terminal extremity of said tubular tutor.

14. The device of claim 12, wherein said front portion comprises threads disposed on said external surface of said front portion, and said rear portion comprises threads disposed on said internal surface of said rear portion.

15. The device of claim 15, wherein said middle portion comprises a plurality of bridges for connecting said front portion with said rear portion, and a circular member connecting said bridges to said front portion.

16. The device of claim 15, wherein said circular member comprises a plurality of notches disposed along the periphery of said circular member, said notches extending toward said rear portion.

17. The device of claim 16, wherein said notches are semi-circular in shape.

18. The device of claim 17, wherein said plurality of bridges comprise two bridges, said two bridges being disposed diametrically opposite to each other and providing, as said holes in said cylindrical wall of each of said plurality of cylindrical sleeves, at least two circumferential slots between said two bridges for receiving said bone-anchoring member therethrough.

19. The device of claim 18, wherein said holes provided in each of said hollow cylindrical members comprise a plurality of diametrically opposed holes, for receiving said bone-anchoring member therethrough to be rotated perpendicularly to said tubular tutor within said one of said two circumferential slots in order to be secured in one of said notches.

20. The device of claim 19, wherein said middle portion comprises a shoulder section provided on said internal surface thereof, said shoulder section being adjacent to said front portion.

21. The device of claim 20, wherein each of said hollow cylindrical members comprises an anterior extremity and a posterior extremity, said anterior extremity abutting said shoulder section and said posterior extremity abutting a front extremity of a successive cylindrical sleeve when said plurality of cylindrical sleeves are releasably connected to form said tubular tutor.

22. The device of claim 21, wherein said diametrically opposed holes are located adjacent to said anterior extremity and away from said posterior extremity.

23. The device of claim 18, wherein the diameter of said semi-circular notches is substantially equal to the diameter of said bone-anchoring member.

24. The device of claim 12, wherein the length of each of said hollow cylindrical members is substantially equal to the length of said middle portion.

25. The device of claim 12, wherein each of said hollow cylindrical members and said middle portion each has an external diameter and an internal diameter, said external diameter of each of said hollow cylindrical members being substantially equal to said internal diameter of said middle portion.

26. The device of claim 12, wherein the diameter of said front portion is substantially equal to the diameter of said rear portion.

27. The device of claim 12, wherein the diameter of said middle portion is greater than the diameter of said front portion.

28. The device of claim 12, wherein the diameter of said middle portion is less than the diameter of said rear portion.

29. The device of claim 12, further comprising a compressor-distracter means for compressing and distracting said cylindrical sleeves.

30. The device of claim 29, wherein said compressor-distracter means comprises:

(a) an elongate axial member comprising an external surface, said external surface having threads thereon;

(b) at least one cylindrically shaped lateral bracket threaded at each end of said elongated axial member; and (c) a first nut fixedly screwed onto said elongate axial member.

31. The device of claim 30, wherein said first nut is substantially centrally positioned so as to divide said elongated axial member into a first section and a second section, each said first section and said second section having threads thereon.

32. The device of claim 31, wherein said threads on said first section spiral in a clockwise direction, and said threads on said second section spiral in a counter-clockwise direction.

33. The device of claim 31, further comprising a second nut screwed on each of said first section and said second section.

34. The device of claim 30, wherein each said lateral bracket comprises a long portion and a short portion, each having a diameter portion wherein the diameter of the short portion is greater than the diameter of said long portion.

35. The device of claim 34, wherein said short portion of a first one of said brackets is adapted to be screwed on said front portion of one of said cylindrical sleeves, and said short portion of a second one of said brackets is adapted to be screwed on said rear portion of another one of said cylindrical sleeves.

* * * * *

UNITED STATES PATENT AND TRADEMARK OFFICE
CERTIFICATE OF CORRECTION

PATENT NO.   : 4,942,872
DATED        : July 24, 1990
INVENTOR(S)  : Roger Jawish It is certified that error appears in the above-identified patent and that said Letters Patent is hereby corrected as shown below:

On the title page item [76] "Robert Jawish" should be --Roger Jawish--.

Signed and Sealed this

Fifth Day of May, 1992

Attest:

DOUGLAS B. COMER

*Attesting Officer*    *Acting Commissioner of Patents and Trademarks*